US00PP26309P2

(12) United States Plant Patent
Kordes

(10) Patent No.: US PP26,309 P2
(45) Date of Patent: Jan. 19, 2016

(54) SHRUB ROSE PLANT NAMED 'KORUMNEZA'

(50) Latin Name: *Rosa hybrida*
Varietal Denomination: KORumneza

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 138 days.

(21) Appl. No.: 13/998,458

(22) Filed: Nov. 1, 2013

(51) Int. Cl.
*A01H 5/02* (2006.01)

(52) U.S. Cl.
USPC ..... Plt./107

(58) Field of Classification Search
USPC ..... Plt./107
See application file for complete search history.

*Primary Examiner* — Keith Robinson

(57) ABSTRACT

A new and distinct variety of rose with long lasting, novel pastel pink flowers, and attractive foliage with excellent disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORumneza'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2002. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORumneza'.

SUMMARY OF THE INVENTION

The new rose plant may be distinguished from its seed parent, an un-named seedling, by the following combination of characteristics:

1. 'KORumneza' has pastel pink flowers, whereas the un-named seedling has deep pink flowers.
2. 'KORumneza' has an upright to bushy growth habit, whereas the un-named seedling has a spreading growth habit.

The new rose plant may be distinguished from its pollen parent, an un-named seedling, by the following combination of characteristics:

1. 'KORumneza' has a semi-double petal count, whereas the un-named seedling has a double petal count.
2. 'KORumneza' has excellent disease resistance, whereas the un-named seedling has average disease resistance.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORumneza' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORumneza' was selected in May 2003 from the seedling beds to be asexually propagated for further evaluation. The first asexual propagation of 'KORumneza' was done by budding in July 2003 at the inventor's nursery in Offenseth-Sparrieshoop, Germany.

These initial and other subsequent propagations conducted in controlled environments demonstrate that 'KORumneza' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORumneza', taken from 2 year old plants.

DETAILED BOTANICAL DESCRIPTION

The following is a description of 'KORumneza', as observed growing in September 2013 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORhopiko', a rose variety from the same inventor described and illustrated in U.S. Plant Pat. No. 23,529 and issued on Apr. 16, 2013 are compared to 'KORumneza' in Chart 1.

CHART 1

| Characteristic | 'KORumneza' | 'KORhopiko' |
|---|---|---|
| Flower color | Pastel pink | Hot pink |
| Flower inflorescence | 2-5 buds per stem | 4-9 buds per stem |
| Blooming habit | Recurrent | Continuous |

Parents:

*Seed parent*.—An un-named seedling.

*Pollen parent*.—An un-named seedling.

Classification:

*Botanical classification*.—*Rosa hybrida* 'KORumneza'.

*Commercial classification*.—Shrub rose.

FLOWER AND FLOWER BUD

Blooming habit: Recurrent.

Inflorescence: In panicles. Each inflorescence consisting of 4-6 laterals that are 30-50 mm length and having 5-7 flower buds. Flowers held upright.

Flower bud:

*Size*.—Upon opening, 35 mm in length from base of receptacle to distal end of bud and 15 mm diameter at its widest point.

*Bud form*.—Long. Pointed ovoid.

*Bud color*.—As sepals first unfold, bud color is Red Group 53A and Red Group 53C. When ¼ open, the upper surface of petals is Red Group 36B, and the lower surface is Red Group 36B with intonations of Red Group 49A. Guard Petals are Red Group 55A and Red Group 55B with intonations of Red Group 53C and Red Group 53D.

*Sepals*.—Color: Upper surface Yellow-Green Group 144B. Lower surface Yellow-Green Group 144A with intonations of Greyed-Purple Group 185B. Size: Average 30 mm (l)×7 mm (w). Shape: Moderate foliaceous appendages on 3 of the five sepals. Apex: Cirrose. Base: Flat at union with receptacle. Quantity: Five. Surface texture: Upper side: Very pubescent. Lower surface: Limited pubescence. Stipitate glands: Abundant numbers along margins.

Flower bloom:

*Fragrance*.—Light.

*Duration*.—On the plant 4 days. Senesced petals drop away cleanly.

*Size*.—Large for a shrub rose. When open, the average flower diameter is 100 mm and the average flower height is 30-35 mm.

*Form*.—Shape of flower when viewed from the side: Upon opening, upper part: Cupped. Upon opening, lower part: Concave. Open flower, upper part: Flat to flattened convex. Open flower, lower part: Concave.

Color:

*Upon opening, petals*.—Outermost petals: Outer Side: Red Group 55D. Inner Side: Red Group 56D to White Group N155B. Innermost petals: Outer Side: Red Group 49C. Inner Side: Red Group 36D.

*Upon opening, basal petal spots*.—Basal petal spot, outermost petals: Outer Side: Green-White Group 157D. Inner Side: Green-Yellow Group 1C. Basal petal spot, innermost petals: Outer Side: Green-White Group 157D. Inner Side: Green-Yellow Group 1D. Average Size: 2.0 mm (l)×2.5 mm (w).

*After opening, petals*.—Outermost petals: Outer Side: Basal zone: White Group 155A. Middle zone: Red Group 55B to Red Group 55C. Marginal zone: Red Group 55A to Red Group 55B. Middle and marginal zones variably darker with exposure to sunlight. Inner Side: Basal zone: White Group 155B. Middle zone: White Group N155C. Marginal zone: Red Group 52A to Red Group 52C. Innermost petals: Outer Side: White Group N155C. Marginal zone: Red Group 49C to Red Group 49D. Inner Side: White Group 155B. Marginal zone: Red Group 49D.

*After opening, basal petal spots*.—Basal petal spot, outermost petals: Outer Side: No distinctive coloration at petal base observed. Inner Side: Yellow Group 2C. Basal petal spot, innermost petals: Outer Side: No distinctive coloration at petal base observed. Inner Side: Green-Yellow Group 1D. Average Size: 2.0 mm (l)×2.5 mm (w).

General tonality: On open flower Red Group 36D. No change in the general tonality at the end of the $2^{nd}$ or $3^{rd}$ day. Afterwards, general tonality is Red Group 38B and Red Group 43D; variably darker with exposure to sunlight.

Petals:

*Petal type*.—Semi Double.

*Petal count*.—Approximately 15 petals under normal conditions.

*Petal reflex*.—Petals reflex somewhat.

*Petal margin*.—Entire.

*Petal shape*.—Obovate. Apex: Obtuse. Base: Cuneate.

*Petal size*.—50 mm (l)×40 mm (w).

*Thickness*.—Average.

*Petal arrangement*.—Not formal.

*Texture*.—Upper: Smooth. Lower: Smooth.

Petaloids:

*Petaloid count*.—Average of 0-2 per flower.

*Petaloid size*.—15-40 mm (l)×5-10 mm (w).

*Petaloid color*.—Inner side: Red Group 38D. Outer side: Red Group 49A.

*Petaloid texture*.—Upper: Smooth. Lower: Smooth.

*Margins*.—Entire.

*Petaloid shape*.—Most commonly spatulate with some petaloids highly irregular. Apex: Emarginate. Base: Attenuate.

Reproductive organs:

*Pistils*.—Average. Approximately 25-30 present. Stigmas: Location: Slightly inferior in position to anthers. Color: Greyed-Yellow Group 160D. Styles: Length:

About 10 mm long. Color: Green-White Group 157D. Ovary Color: White Group 155A. Length: 7 mm. Diameter: 5 mm.

*Stamens*.—Approximately 100-120 on average and regularly arranged. Anthers: Size: Average 3 mm (l)×1 mm (w). Color: Greyed-Yellow Group 160D. Pollen: Generally present in moderate amounts. Color: Greyed-Orange Group N163D. Filaments: Color: Yellow Group 3C. Length: 12 mm.

*Receptacle*.—Surface: With fine hairs. Color: Yellow-Green Group 144A with intonations of Greyed-Purple Group 185A. Shape: Urn-shaped. Texture: Smooth. Size: 8 mm (h)×7 mm (w).

*Pedicel*.—Surface: With fine hairs and stipitate glands. Length: 25-30 mm average length. Diameter: 3-4 mm average diameter. Color: Yellow-Green Group 144B with intonations of Greyed-Purple Group 187C. Strength: Strong. Texture: Smooth.

*Peduncle*.—Length: 25-40 mm average length. Diameter: 3-4 mm average diameter. Color: Yellow-Green Group 144B with intonations of Greyed-Purple Group 187C. Strength: Strong. Texture: Smooth.

THE PLANT

Growth: Moderate.

Plant habit: Upright to bushy. When grown as a field plant, the average plant height is 75 cm and the average plant width is 45 cm.

Stems:

*Stem color*.—Young Wood: Yellow-Green Group 144A. Older wood: Green Group 138A.

*Intonations*.—Greyed-Purple Group 185A.

*Stem surface texture*.—Young wood: Smooth. Older wood: Smooth.

Prickles: Present.

*Incidence*.—Average of 5-7 per each 10 cm of stem.

*Size*.—Average length: 4 mm.

*Color*.—Immature prickles: Greyed-Purple Group 187C. Mature prickles: Yellow-Green Group 145D.

*Shape*.—Deeply concave.

*Texture*.—Smooth.

Leaves: Normally 5 leaflets on normal leaves in middle of the stem.

*Venation pattern*.—Pyramidal net pattern.

*Leaf size*.—100 mm (l)×90 mm (w).

*Shape*.—Elliptic.

*Abundance*.—Very abundant.

*Texture*.—Upper side of leaf: Smooth. Under side of leaf: Smooth.

Leaflets:

*Size*.—Average size of the terminal leaflet is 55-60 mm (l)×30-35 mm (w).

*Shape*.—Elliptic to ovate. Base: Obtuse. Apex: Acute.

*Margins*.—Serrated.

*Surface*.—Upper side of leaflet: Glossy. Under side of leaflet: Matte.

*Texture*.—Upper side of leaflet: Leathery. Under side of leaflet: Leathery.

*Color, mature foliage*.—Upper Leaflet Surface: Green Group 139A. Lower Leaflet Surface: Green Group 137C.

*Color, juvenile foliage*.—Upper Leaflet Surface: Yellow-Green Group 146A. Lower Leaflet Surface: Yellow-Green Group 147B.

*Anthocyanin intonation*.—Greyed-Purple Group 187A. Location: Upper and lower sides of juvenile foliage.

*Arrangement*.—Odd pinnate.

*Venation*.—Reticulate.

Stipules:

*Size*.—15 mm (l)×11 mm (w).

*Stipule color*.—Yellow-Green Group 144A.

*Stipitate glands*.—Abundant numbers along margins and under side.

*Texture*.—Smooth.

*Shape*.—Apex: Apiculate. Base: Flat.

Petiole:

*Length*.—Average 17 mm.

*Diameter*.—Average 2 mm.

*Petiole color*.—Yellow-Green Group 146B. Underneath: Yellow-Green Group 146C.

*Anthocyanin*.—Greyed-Purple Group 183B.

*Prickles*.—None observed.

*Stipitate glands*.—Abundant numbers along margins.

*Texture*.—Smooth.

Petiole rachis:

*Length*.—Average 14 mm.

*Diameter*.—Average 1.5 mm.

*Color*.—Yellow-Green Group 146B. Antbocyanin present on juvenile tissue: Greyed-Purple Group 183B.

*Prickles*.—A few small prickles underneath.

*Stipitate glands*.—Limited numbers along margins.

*Texture*.—Smooth.

Root:

*Type*.—Fibrous.

*Color*.—Brown Group 200C.

Hips/seed formation: None observed.

Winter hardiness: To date, the variety has been grown successfully in Zones 6-9.

Disease resistance: Excellent resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

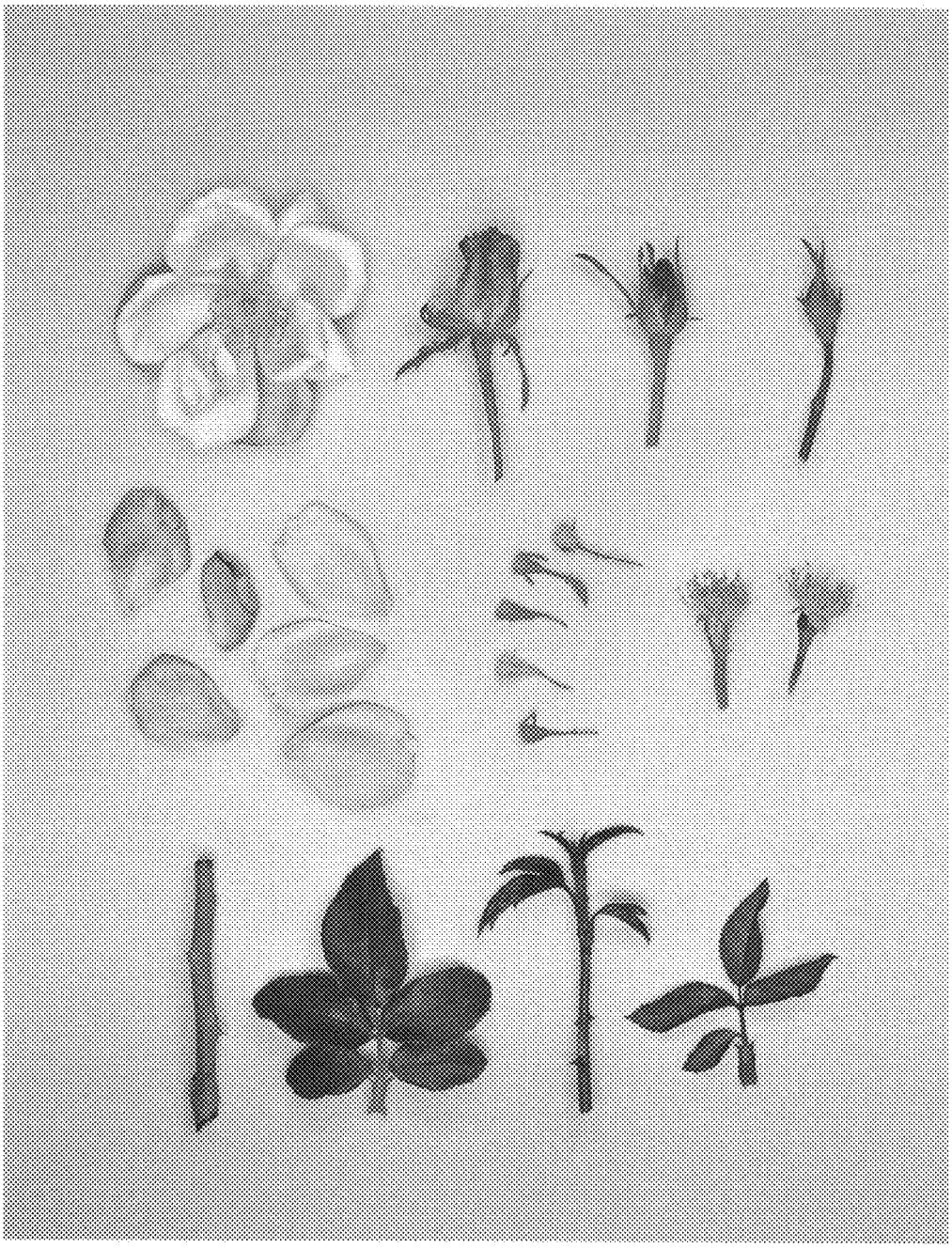

* * * * *